United States Patent [19]

Zaima et al.

[11] Patent Number: 5,880,313
[45] Date of Patent: Mar. 9, 1999

[54] PROCESS FOR PRODUCING AROMATIC CARBOXYLIC ACID

[75] Inventors: Fumiya Zaima; Hideaki Fujita; Masami Matsumoto; Masato Inari, all of Okayama-ken, Japan

[73] Assignee: Mitsubishi Gas Chemical Company, Inc., Tokyo, Japan

[21] Appl. No.: 139,677

[22] Filed: Aug. 25, 1998

[30] Foreign Application Priority Data

Sep. 9, 1997 [JP] Japan .................................. 9-244043

[51] Int. Cl.$^6$ .................................................. C07C 51/16
[52] U.S. Cl. ............................................................ 562/414
[58] Field of Search .............................................. 562/414

[56] References Cited

U.S. PATENT DOCUMENTS 4,162,991  7/1979  Jones ........................................ 562/414
4,317,919  3/1982  Jones et al. .............................. 562/414
5,731,466  3/1998  Kida ........................................ 562/414

*Primary Examiner*—Samuel Barts
*Attorney, Agent, or Firm*—Frishauf, Holtz, Goodman, Langer & Chick, P.C.

[57] ABSTRACT

A process for continuously producing an aromatic carboxylic acid comprising oxidizing an aromatic compound substituted with alkyl groups with molecular oxygen gas in the liquid phase in a solvent containing a lower aliphatic carboxylic acid in the presence of a catalyst comprising heavy metal compounds and a bromine compound, wherein a mother liquor which is obtained after removal of crystals from a reaction liquid of the liquid phase oxidation and contains heavy metal ions and bromine ion as catalyst components is brought into contact with a chelate resin of an anion exchange type to recover the catalyst components.

The catalyst components are efficiently recovered, and auxiliary agents in an amount exceeding the equivalent amount and excessive labor are not necessary.

9 Claims, 1 Drawing Sheet

PROCESS FOR PRODUCING AROMATIC CARBOXYLIC ACID

BACKGROUND OF THE INVENTION

1. Field of the Invention

The present invention relates to process for producing an aromatic carboxylic acid. More particularly, the present invention relates to a process for producing an aromatic carboxylic acid, particularly 2,6-naphthalenedicarboxylic acid, by the liquid phase oxidation of an aromatic compound substituted with alkyl groups, wherein catalyst components are efficiently recovered from a mother liquor obtained after separation of crystals from the reaction liquid of the liquid phase oxidation.

2. Description of the Related Arts

Aromatic carboxylic acids, particularly aromatic dicarboxylic acids such as terephthalic acid and 2,6-naphthalenedicarboxylic acid, and esters thereof are useful as raw materials for polyesters which are used as fibers and resins.

Aromatic carboxylic acids are produced by liquid phase oxidation of aromatic compounds substituted with alkyl groups in the presence of a heavy metal catalyst. For example, in processes proposed in the specifications of Japanese Patent Publication Showa 34(1959)-2666 and Japanese Patent Publication Showa 56(1981)-3337, an aromatic dicarboxylic acid is obtained by oxidation in a solution containing a lower aliphatic carboxylic acid in the presence of a catalyst containing a heavy metal, such as cobalt and manganese, and bromine.

In the above processes, the reaction product is obtained in the form of a slurry containing solid substances after the oxidation, and the aromatic carboxylic acid is obtained from crystals separated by solid-liquid separation of the slurry. The mother liquor which is obtained as the filtrate after the solid-liquid separation of the slurry contains useful catalyst components, such as expensive heavy metals such as cobalt and manganese and bromine compounds. It is necessary that the catalyst components be recycled in order to use these components efficiently.

The simplest method for the recycling is to reuse the mother liquor without any treatment. However, various organic impurities formed as byproducts in the reaction and inorganic substances formed by elution of materials of apparatuses are present in the mother liquor. These impurities are concentrated during the recycling and occasionally have serious adverse effects on the oxidation.

Therefore, the direct recycling of the mother liquor is limited, and catalyst components which are not reused by the recycling of the mother liquor must be recovered. Various processes have heretofore been proposed to recover catalyst components which are not reused by the recycling of a mother liquor.

For example, water and an alkali metal carbonate are added to a residue obtained after removal of a solvent from a mother liquor, and metal components of a catalyst are precipitated in the form of carbonates, which are then dissolved in acetic acid to recover the metal components (Japanese Patent Application Laid-Open No. Showa 48(1973)-66090). In another example, oxalic acid is added to a mother liquor which is not recycled, and metal components of a catalyst are recovered as oxalates (Japanese Patent Application Laid-Open No. Heisei 2(1990)-203939).

It has been known that metal components can be recovered with anion exchange resins from a mother liquor which is not recycled. For example, cobalt and bromine in the mother liquor is adsorbed with a strong basic anion exchange resin after the ratio of bromine to cobalt has been adjusted in a specific range, and the adsorbed cobalt and bromine are eluted with acetic acid containing water to recover organic substances containing cobalt (Japanese Patent Application Laid-Open No. Showa 53(1978)-133574). In another example, a mother liquor is first brought into contact with an anion exchange resin in the bromide form so that heavy metals are adsorbed with the anion exchange resin, and the adsorbed heavy metals are subsequently recovered from the ion exchange resin by elution. The treated mother liquor is then brought into contact with a weak basic anion exchange resin so that bromine ion is adsorbed with the anion exchange resin, and the adsorbed bromine ion is subsequently recovered by elution from the anion exchange resin (Japanese Patent Application Laid-Open No. Showa 53(1978)-104590).

When metal components are recovered as carbonates or oxalates, auxiliary agents such as alkali metal carbonates and oxalic acid are necessary in amounts exceeding the equivalent amounts, and the processes are not economically advantageous. Moreover, recovery of the carbonates and oxalates requires complicated operations such as neutralization, precipitation and separation of metal salts and excessive labor.

The processes using an anion exchange resin are superior to the above processes in that such agents are not necessary. However, in order to achieve complete adsorption of heavy metals, bromine ion is necessary in an amount by mol about twice or more as much as the amount of the heavy metal at the time of the adsorption. The bromine ion is recovered simultaneously when the heavy metals are recovered. Therefore, the ratio of bromine ion and the heavy metal components in the oxidation is naturally restricted, and the oxidation is conducted in the presence of a large relative amount of bromine ion.

Although it is necessary that the ratio of bromine ion to heavy metals be kept at a specific value or more in the oxidation, bromine ion in an excessively large amount does not show further contribution to the improvement of the reaction, and the amount of bromine discharged to the outside of the system as organic bromine compounds in the off-gas increases. This causes loss of bromine, and the possibility of corrosion also increases. Therefore, it is not preferable that the ratio of bromine ion to heavy metals in a catalyst must be kept at a high value in the liquid phase oxidation.

In the processes using carbonates and oxalates, the metal components are concentrated to form solid substances. In contrast, metals adsorbed with an anion exchange resin are recovered by elution with acetic acid containing a large amount of water. The degree of concentration of the eluted ions is decided by the concentration during the elution, and occasionally the degree of concentration of the eluted ions is insufficient. When the degree of concentration of eluted ions is insufficient, recycling of the recovered catalyst directly into the reaction system increases the concentration of water in the reactor, and this adversely affects the reaction. Therefore, an additional treatment such as removal of water before the recycling is necessary, and this consumes additional energy.

SUMMARY OF THE INVENTION

The above drawbacks of the conventional technologies are improved by the present invention. An object of the present invention is to provide a process which enables efficient recovery of catalyst components with an anion exchange resin without using an auxiliary agent in an amount exceeding the equivalent amount and without complicated operations or excessive labor in a process for continuously producing an aromatic carboxylic acid by liquid phase oxidation of an aromatic compound substituted with alkyl groups in a lower aliphatic carboxylic acid as the solvent in the presence of a catalyst comprising heavy metal compounds and a bromine compound.

As the result of extensive studies by the present inventors to achieve the above object in the production of an aromatic carboxylic acid, it was found that, when a chelate resin of an anion exchange type is used as the anion exchange resin, the desirable effect can be exhibited independently of the ratio of bromine ion to the heavy metal ions during adsorption and that the catalyst components are efficiently recovered and the liquid phase oxidation can be carried out advantageously without operations for the oxidation at a larger ratio of bromine ion to the heavy metal ion or for separation of water. The present invention has been completed on the basis of the above knowledge.

Accordingly, the present invention provides a process for continuously producing an aromatic carboxylic acid comprising oxidizing an aromatic compound substituted with alkyl groups with molecular oxygen gas in the liquid phase in a solvent containing a lower aliphatic carboxylic acid in the presence of a catalyst comprising heavy metal compounds and a bromine compound, wherein a mother liquor which is obtained after removal of crystals from a reaction liquid of the liquid phase oxidation and contains heavy metal ions and bromine ion as catalyst components is brought into contact with a chelate resin of an anion exchange type, and subsequently, the catalyst components are recovered with an elution liquid.

It was also found by the present inventors that the catalyst components can efficiently be recovered in the following preferred embodiments of the present invention.

(1) The mother liquor is brought into contact with the chelate resin at a temperature of 50° to 120° C. and the elution liquid is brought into contact with the chelate resin at a temperature of 20° to 60° C.

(2) The mother liquor is brought into contact with the chelate resin of an anion exchange type in an ion exchange column so that the heavy metal ions and the bromine ion of the catalyst components are adsorbed with the chelate resin, and subsequently, the elution liquid is passed through the ion exchange column in the direction opposite to the direction of the mother liquor.

(3) After the mother liquor is brought into contact with the chelate resin of an anion exchange type so that the heavy metal ions and the bromine ion are adsorbed with the chelate resin, the liquid remaining in a layer of the chelate resin is replaced with an inert gas.

Particularly when 2,6-naphthalenedicarboxylic acid is produced, an auxiliary agent such as an alkali metal carbonate and oxalic acid is used in a large amount in order to recover the metal components as carbonates or oxalates because the concentration of heavy metal ions in the mother liquor of the oxidation is relatively high. Therefore, an anion exchange resin can be used effectively, and the catalyst components can be efficiently recovered by the combination of (1) and (2).

Accordingly, the present invention also provides a process for continuously producing 2,6-naphthalenedicarboxylic acid comprising oxidizing a 2,6-dialkylnaphthalene with molecular oxygen gas in the liquid phase in a solvent containing a lower aliphatic carboxylic acid in the presence of a catalyst comprising heavy metal compounds and a bromine compound, wherein a mother liquor which is obtained after removal of crystals from a reaction liquid of the liquid phase oxidation and contains heavy metal ions and bromine ion as catalyst components is brought into contact with an anion exchange resin at 50° to 120° C., and subsequently, the catalyst components are recovered by passing an elution liquid through the chelate resin in a direction opposite to the direction of the mother liquor at 20° to 60° C.

Figure 1:
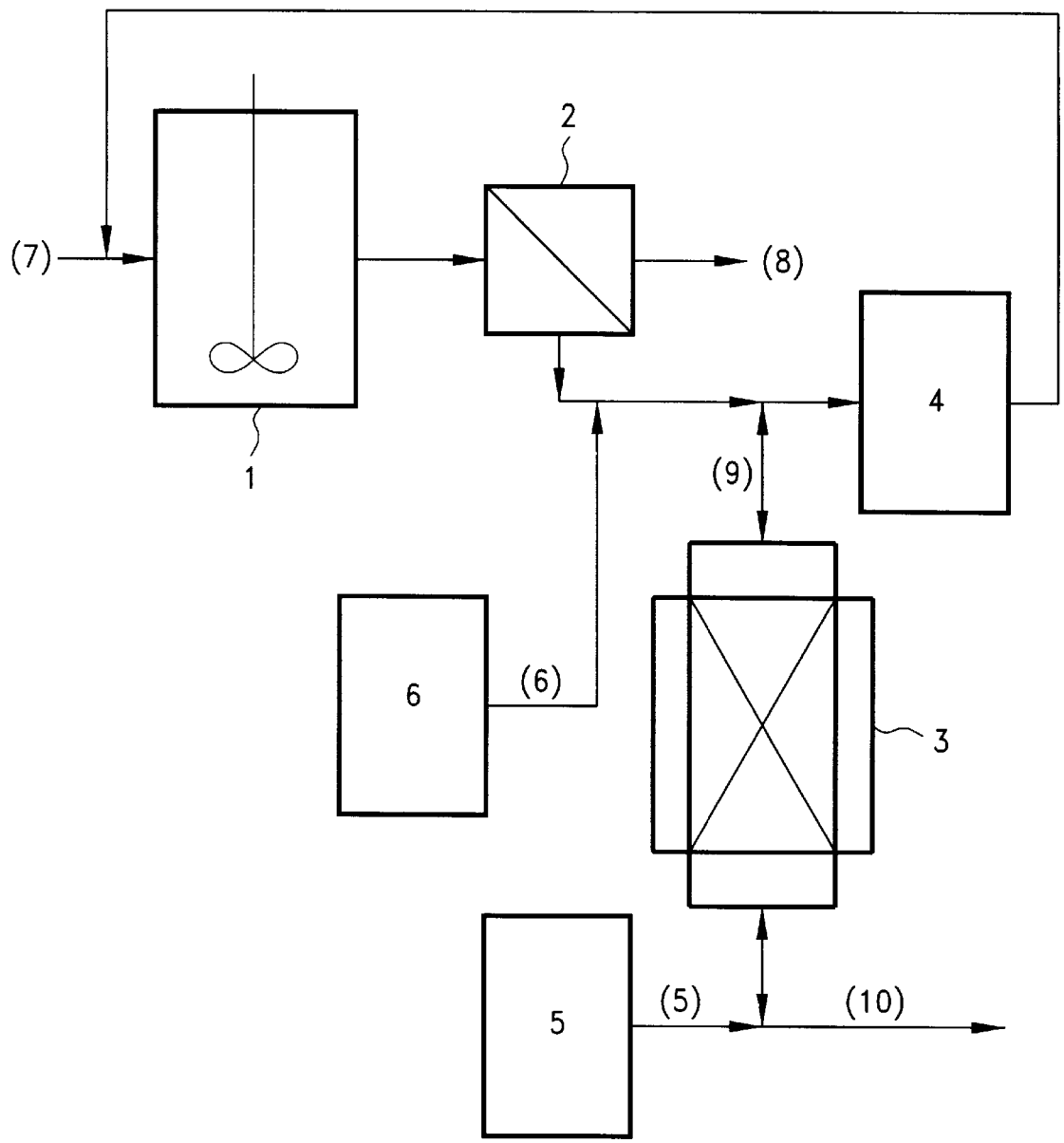
FIG. 1 shows a schematic flow chart exhibiting an example of the process for producing an aromatic carboxylic acid of the present invention. In this flow chart, a mother liquor of the oxidation is passed through an ion exchange column downward from an upper part of the column, and an elution solution is passed through the ion exchange column upward from a lower part of the column.

Numbers in FIG. 1 have the following meanings:

1: A reactor of the liquid phase oxidation
2: A solid-liquid separator
3: An ion exchange column
4: An intermediate tank
5: An elution liquid tank

DESCRIPTION OF THE PREFERRED EMBODIMENTS

Examples of the aromatic compound substituted with alkyl groups which is used as the raw material of the oxidation in the present invention include toluene, p-xylene, m-xylene, pseudocumene, 2,6-dimethylnaphthalene, 2,6-diethylnaphthalene and 2,6-diisopropylnaphthalene. From these aromatic compounds, aromatic carboxylic acids such as benzoic acid, terephthalic acid, isophthalic acid, trimellitic acid and 2,6-naphthalenedicarboxylic acid are produced. The process of the present invention is particularly advantageously used for producing 2,6-naphthalenedicarboxylic acid by the reason described above.

Examples of the lower aliphatic carboxylic acid used as the solvent of the oxidation in the present invention include formic acid, acetic acid, propionic acid, butyric acid and mixtures of these acids. Acetic acid is preferable among these acids from the standpoint of heat stability. The solvent may contain water. The content of water is preferably 30% by weight or less. The amount by weight of the solvent is 1 to 20 times, preferably 2 to 10 times, as large as the amount by weight of the aromatic compound substituted with alkyl groups which is the raw material of the oxidation. When the amount of the solvent is less than the above range, handling of the slurry of the reaction product occasionally becomes difficult. When the amount of the solvent exceeds the above range, the burned amount per the amount of the product occasionally increases to cause economic disadvantage.

In the present invention, heavy metal compounds and a bromine compound are used for the oxidation catalyst. The heavy metal compounds comprise at least one compound selected from the group consisting of cobalt compounds and manganese compounds. Compounds of nickel, cerium or zirconium may be added, where necessary. Examples of the compounds of cobalt, manganese and other heavy metals include salts of organic acids, hydroxides, halides and carbonates of these metals. Acetates and bromides are preferably used. As the bromine compound, any compound containing bromine can be used as long as the compound is soluble in the reaction system and generates bromine ion. Examples of the bromine compound include inorganic bromine compounds such as hydrogen bromide, sodium bromide and cobalt bromide and organic bromine compounds such as bromoacetic acid and tetrabromoethane. Hydrogen bromide, cobalt bromide and manganese bromide are preferably used.

As for the amount of the catalyst containing the heavy metals, the cobalt compound and/or the manganese compound is added to a solvent in such an amount that the total concentration of the metal atoms is in the range of 0.01 to 1.5% by weight. When the amount of the catalyst containing the heavy metals is less than the above range, occasionally, a sufficient activity is not obtained. When the amount of the catalyst exceeds the above range, the amount of the catalyst removed together with the crystals of the formed aromatic dicarboxylic acid increases, and the process becomes industrially disadvantageous because of an increase in cost of the catalyst.

The bromine compound is added in such an amount that the ratio by atom of bromine to the total amount of the metals in the catalyst is 0.1 to 10, preferably 0.5 to 5. When the amount of the bromine compound is less than the above range, occasionally, a sufficient activity is not obtained. When the amount of the bromine compound exceeds the above range, the amount of bromine discharged in the off-gas in the form of organic bromine compounds increases to increase loss of bromine, and the possibility of corrosion also increases. Therefore, such amounts are not preferable.

In the present invention, the aromatic compound substituted with alkyl groups is oxidized with molecular oxygen. Oxygen gas or a gas containing oxygen and an inert gas such as nitrogen and argon is used for the reaction. The air is generally used.

The reactor used for the oxidation may be a reactor equipped with a stirrer or a gas atomizer. A reactor equipped with a stirrer is preferably used because sufficient mixing of the content can be achieved.

The reaction is conducted in a continuous production apparatus. The reaction may be completed in a single step. However, it is preferable that a plurality of reactors connected in series are used to increase the yield of the reaction.

The temperature of the liquid phase oxidation in the present invention is in the range of 170° to 250° C., preferably 180° to 240° C. When the temperature is lower than the above range, large amounts of intermediate products of the reaction remain in the product. When the temperature exceeds the above range, loss of the solvent by burning increases.

The pressure of the reactor is not particularly limited as long as the reaction system is kept in the liquid phase at the temperature of the reaction. The pressure is generally 5 to 40 kg/cm$^2$, preferably 10 to 30 kg/cm$^2$.

In the oxidation, the gas containing oxygen is continuously supplied to the reactor, and the gas which has been used for the reaction is continuously discharged to the outside of the reactor as an off-gas. A reflux condenser is attached to the reactor to condense a large amount of the solvent accompanied with the off-gas and water formed by the oxidation. The condensed solvent and water are generally returned to the reactor. However, a portion of the condensed liquid may occasionally be taken out of the reaction system to adjust the concentration of water in the reactor.

In the process of the present invention, the amount of the gas containing oxygen which is supplied to the reactor is adjusted so that the concentration of oxygen gas is in the range of 0.5 to 5% by volume in the off-gas discharged from the reactor as a dry gas from which water and the solvent have been removed by condensation. When the concentration of oxygen in the off-gas is lower than the above range, the amounts of intermediate products increase and, moreover, undesirable phenomena such as coloring of the formed aromatic dicarboxylic acid may occasionally take place. When the concentration of oxygen exceeds the above range, loss of the lower aliphatic carboxylic acid used as the solvent by oxidation increases, and the cost of an air compressor increases unnecessarily.

It is preferable that the reaction liquid containing crystals of the aromatic carboxylic acid formed in the oxidation reactor is transferred to another oxidation reactor connected to the first reactor in series, and the oxidation is completed with the gas containing oxygen in the second reactor. Where necessary, the resultant reaction liquid is transferred to one or more crystallization tanks connected in series. The obtained product is cooled after the pressure was released and then transferred to the next solid-liquid separation step.

In the solid-liquid separation step, the slurry formed by the oxidation and containing the aromatic carboxylic acid is separated into crystals and a mother liquor by a solid-liquid separator. The separation of the crystals is generally carried out under an atmospheric pressure. The temperature of the separation is not particularly limited. The separation is carried out generally at a temperature lower than the boiling point of the solvent under an atmospheric pressure, for example in the range of about 50° to 110° C.

Examples of the separator include a centrifugal sedimentation separator, a centrifugal filter and a vacuum filter.

In the process of the present invention, the mother liquor of the oxidation containing heavy metals such as cobalt, manganese and bromine, which is obtained after separation of crystals from the reaction liquid of the liquid phase oxidation as described above, is brought into contact with a resin of an ion exchange type by passing the mother liquor through an ion exchange column, and subsequently the catalyst components are recovered with an elution liquid. After the mother liquor of the oxidation is brought into contact with the resin, a portion of the mother liquor may be returned directly to the reactor of the oxidation. Where necessary, a portion or the entire amount of the mother liquor may further be treated with an anion exchange resin. The crystals separated by the solid-liquid separator may be washed with water or acetic acid containing water. The liquid produced by the washing may be added to the mother liquor of the oxidation, and the resultant mixture may be passed through a column of an ion exchange resin.

The mother liquor of the oxidation which is treated by the ion exchange column in the present invention (occasionally, referred to hereinafter as a liquid for treatment) is a mixture containing the aromatic carboxylic acid, the solvent, the catalyst, various organic compounds, such as the unreacted raw material and intermediate products and byproducts of the reaction, and water formed by the reaction in a considerable amount. The content of fine crystals in the liquid for treatment is 1.0% by weight or less, preferably 0.1% by weight or less. The solid-liquid separation is conducted so as to bring the content of fine crystals within this range.

In the process of the present invention, it is particularly preferable that a chelate resin of an anion exchange type is used as the anion exchange resin. The chelate resin is an ion exchange resin exhibiting a particularly high selectivity to specific metal ions by forming the chelate bonding. Examples of the chelate resin of an anion exchange type include chelate resins of the picolylamine type, the polyamine type, and the pyridine type. Any of these resins can be used. Specific examples of the chelate resin include UNISELEC UR-3300S (a trade name; manufactured by UNITICA Co., Ltd.), DIAION CR20 (a trade name; manufactured by MITSUBISHI CHEMICAL Co., Ltd.), SUMICHELATE CR-2 (a trade name; manufactured by SUMITOMO CHEMICAL Co., Ltd.) and DOWEX XFS 4195 (a trade name; manufactured by DOW CHEMICAL Company).

It is the characteristic of the present invention that, among various anion exchange resins, a chelate resin of an ion exchange type is used.

When a heavy metal is adsorbed with an ordinary anion exchange resin, the metal atom has several bromine atoms coordinated with the metal atom. When the number of the bromine atom coordinated with the metal atom is smaller, the metal atom is not adsorbed because of insufficient stability. Therefore, it is generally necessary that the ratio of bromine ion to the metal atom of the catalyst (referred to hereinafter as a bromine ratio) in the liquid for the treatment be two or more.

In contrast, the restriction by the bromine ratio is not necessary when the chelate resin of an ion exchange type, which is a characteristic component in the present invention, is used. The reasons are considered to be that (1) a ligand other than bromine such as acetate ion and hydroxy ion can be selected when the chelate resin of an ion exchange type is used, and that (2) the metal ion adsorbed with the chelate resin has, as the ligands, two or more bromine atoms which are present in the chelate resin by the ion exchange. The chelate resins have a characteristic that an adsorbed ion forms a cyclic structure with a multidentate ligand having two or more coordinating atoms, i.e., a chelate compound, unlike ordinary ion exchange resins in which an ion is adsorbed at a single coordinating site. Therefore, the latter phenomenon (2) is considered to be more likely to be the reason.

By passing the mother liquor of the oxidation through the ion exchange resin, cobalt, manganese and bromine of the catalyst components are selectively adsorbed. Because other metal impurities are only negligibly adsorbed by the above ion exchange resin, cobalt, manganese and bromine of the catalyst components can be simultaneously recovered by passing an elution liquid through the resin and can be recycled as the catalyst for the oxidation.

The ion exchange resin may be used for a liquid for the treatment without any pretreatment. However, it is preferable that the resin is brought into contact with a solution, such as an acetic acid solution, containing bromine and converted into the bromide form in advance.

To convert the ion exchange resin into the bromide form, the resin is washed with water or a solution of acetic acid which contains bromine ion, for example, as sodium bromide or hydrobromic acid, and, thereafter, excess bromine is removed by washing with acetic acid or acetic acid containing 15% by weight or more of water. It is preferable that acetic acid used for the washing has a smaller concentration of water than that of the mother liquor of the reaction which is the liquid for treatment.

In the present invention, the concentration of water in the liquid for treatment passed through the ion exchange column is 0 to 15% by weight, preferably 5 to 12% by weight. In general, the mother liquor of the oxidation contains 5 to 10% by weight of water, and the adjustment of the concentration of water is not necessary before the mother liquor is supplied to the ion exchange column in many cases. When a liquid produced by washing the crystals is added to the mother liquor as described above and the concentration of water in the mother liquor exceeds the above range, the concentration of water is adjusted into the above range by distillation or the like method.

The elution liquid which is used for elution and recovery of the metals adsorbed with the ion exchange resin is preferably water or an aliphatic carboxylic acid containing water. The same solvent as that used for the oxidation is used as the elution liquid. Acetic acid is generally used. The concentration of water in acetic acid is 15% by weight or more, preferably 25% by weight or more. The condensed liquid separated in the reflux cooler of the reactor of the oxidation may be used as the elution liquid.

The temperature of the liquid for treatment is in the range of 50° C. to 120° C., preferably in the range of 70° to 110° C., when the liquid is brought into contact with the anion exchange resin. A temperature exceeding the above range is not preferable because a higher temperature has restriction due to heat resistance of the anion exchange resin and the boiling point of the solvent (acetic acid). When the temperature is lower than this range, the activity of adsorption of the anion exchange resin occasionally decreases.

The temperature of the elution solution during recovery of the catalyst components is selected in the range of 20° to 60° C., preferably 30° to 50° C. When the temperature is higher than this range, the efficiency of the elution may decrease because the activity of adsorption of the resin is higher. When the temperature is lower than this range, the cost of cooling increases. Therefore, such temperatures are not preferable.

In the present invention, it is preferable that the temperature of the mother liquor which is in contact with the anion exchange resin is kept at a relatively high temperature, i.e., a temperature in the range of 50° to 120° C., preferably in the range of 70° to 110° C., and the temperature of the elution liquid used for recovery of the catalyst components is kept at a relatively low temperature, i.e., a temperature in the range of 20° to 60° C., preferably in the range of 30° to 50° C., to achieve more efficient recovery of the catalyst components. This is one of the characteristics of the present invention found by the present inventors.

The above characteristic is based on the fact that the equilibrium between the concentration of the metal ion adsorbed with the anion exchange resin and the concentration of the metal ion in the solution changes with the temperature to a great degree. In other words, at a high temperature of the environment, the activity of adsorption of the anion exchange resin is high and the condition is relatively advantageous for adsorption; on the other hand, at a low temperature of the environment, the activity decreases and the condition is relatively advantageous for elution; and the above characteristic is based on this fact.

A system using an anion exchange resin is essentially a system in which adsorption and desorption are repeated utilizing the difference in stability of a substance for adsorption which is obtained by changing the concentration of water in the solvent. The swing of the temperature such as that described above can effectively be applied for chelate resins.

The system in which the temperature is changed between adsorption and desorption is well known for conventional adsorbents as the temperature swing system for repeated absorption and desorption. The pressure swing system is also well known. However, such systems are not generally known for a process using an ion exchange resin.

It is effective for more fully exhibiting the function of the system of the present invention that the heavy metal ions and bromine ion of the catalyst components are adsorbed with the anion exchange resin by passing the mother liquor through the ion exchange resin, and then the catalyst components are recovered by passing the elution solution through the ion exchange resin in a direction opposite to the direction of the mother liquor of the oxidation. Particularly, it is preferable that the mother liquor of the oxidation is passed through the ion exchange resin downward from the upper part of the ion exchange column, and the elution liquid is passed through the column upward from the lower part of the column.

It is also one of the characteristics of the present invention found by the present inventors that the direction of flow of the mother liquor of the oxidation is made opposite to the direction of flow of the elution liquid.

In the process for recovery of the catalyst components using an anion exchange resin reported in Japanese Patent Application Laid-Open No. Showa 53(1978)-104590, which is described above as the conventional process, a mother liquor of the liquid phase oxidation is supplied at the top of an ion exchange column so that the catalyst components are adsorbed, and then an elution liquid is supplied at the top of the ion exchange column to recover the metals of the catalyst components. In accordance with this process, there is the tendency that the catalyst components adsorbed in low concentrations are first eluted and recovered, and the concentrations of the recovered catalyst components gradually increase.

In contrast, in the present invention, the catalyst components adsorbed in high concentrations are first eluted and recovered because the elution liquid is passed through the column in the direction opposite to the mother liquor of the oxidation. When the yield of recovery in the same period of time are compared between these processes, it is apparent that the process of the present invention can achieve a higher yield of recovery of the catalyst components.

In the present invention, it is preferable that the mother liquor of the oxidation is passed through the ion exchange column downward from the upper part of the column, and the elution solution is passed through the column upward from the lower part of the column. When the directions of the liquids are selected in this manner, the catalyst components which are adsorbed in high concentrations at upper parts of the ion exchange column can be eluted first, and the elution and recovery of the catalyst components can be carried out more efficiently than the case in which the elution liquid is passed through the column downward from the upper part of the column.

Moreover, when the mother liquor of the oxidation is passed through the ion exchange column downward from the upper part of the column, and the elution solution is passed through the column upward from the lower part of the column as described above, crystals of the aromatic carboxylic acid and organic impurities which have leaked through the solid-liquid separation or are precipitated because of decrease in the temperature of the mother liquor are discharged from the upper part of the ion exchange column during the elution. Thus, accumulation of such crystals and impurities can be prevented.

Therefore, problems, such as troubles in operation accompanied with increase in the pressure difference caused by the accumulation described above, decrease in the ability of exchange caused by adhesion of the crystals and organic impurities described above to the surface of the ion exchange resin and decrease in the adsorbing ability caused by uneven flow in the inner parts of the resin due to the migrated crystals, can be prevented by adopting the above method of passing the liquids. Passing the eluting liquid through the column upward from the lower part of the column has a further advantages that the ion exchange resin which has been pressed into a tight condition can be relaxed to a loose condition.

When the elution liquid is passed through the column upward from the lower part of the column, the operation is made at a low space velocity (SV) or a structure working as a stopper is formed at an upper part of the resin layer in order to prevent pulverization of the resin.

It is effective for removing organic impurities attached to the resin that acetic acid containing water in the same concentration as that of the mother liquor or lower is passed through the column from the upper part or the lower part of the column between the operations of the adsorption and the elution. The yield of recovery of the catalyst components can also be increased.

The present invention will be described more specifically with reference to a figure showing a schematic flow chart of the process in the following. FIG. 1 shows an example of the process in which the mother liquor of the oxidation is passed through the ion exchange column downward from the upper part of the column, and the elution liquid is passed through the column upward from the lower part of the column. In FIG. 1, a mixture of raw materials 7 is transferred to a reactor of the liquid phase oxidation 1 to carry out the oxidation. The reaction liquid obtained by the liquid phase oxidation is a slurry containing the aromatic carboxylic acid of the reaction product. The reaction liquid is separated into a solid and a liquid in a solid-liquid separator 2, and a cake of crystals of crude aromatic dicarboxylic acid 8 is obtained.

In the adsorption step, a mother liquor of the reaction obtained by the separation is supplied at the upper part 9 of an ion exchange column 3. In the ion exchange column 3, the supplied mother liquor is sufficiently heat insulated so that the temperature of the elution liquid is kept unchanged by the outside temperature.

In the ion exchange column 3, ions of cobalt, manganese, and bromine contained in the mother liquor are separated by adsorption simultaneously. Organic compounds such as organic impurities and metal impurities other than cobalt and manganese are not adsorbed and purged through the passage 10 at the lower part of the column together with the reaction liquid of the oxidation.

In the elution step, cobalt, manganese and bromine adsorbed in the ion exchange column are simultaneously eluted by passing an elution liquid 6, such as an aqueous solution of acetic acid, through the column upward from the lower part of the column. The elution solution used here is supplied from an elution liquid tank 5. The aqueous solution of acetic acid which flows out of the top of the column and contains eluted cobalt, manganese and bromine is collected into an intermediate tank 4 and recycled to utilize the catalyst again for the liquid phase oxidation.

In the present invention, it is preferable that the liquid remaining in the ion exchange layer after the adsorption has been completed is replaced with an inert gas. Nitrogen or carbon dioxide can be used as the inert gas. A gas discharged from the oxidation step can also be used as the inert gas. The ion exchange resin in which the remaining liquid has been replaced with the inert gas is used in the elution step. It is preferable that the elution liquid is supplied upward from the lower part of the column. When a liquid is supplied into a column containing pores downward from the upper part of the column, there is the possibility that bubbles are contained in the liquid. When the liquid is supplied upward, this possibility can be eliminated.

It is also one of the characteristics of the present invention found by the present inventors that the liquid remaining in the column of the ion exchange resin is replaced with an inert gas after the adsorption of the metal ions and bromine ion with the chelate resin of an anion exchange type have been completed.

The liquid remaining in the resin layer immediately after the adsorption has been completed is the mother liquor from which the metal ions and bromine ion have been removed by the adsorption, and this mother liquor naturally contains metals and water in low concentrations. When the column is switched to elution immediately after the adsorption is completed, the liquid remaining in the resin layer is mixed with the elution liquid, and the elution liquid is diluted. Moreover, it is delayed that the concentration of water in the liquid in the inner part of the resin layer reaches the desirable value for the elution. These phenomena are not preferable for concentration of the catalyst components.

To solve the above problems, the elution liquid may be used after a suitable interval of time from the end of the adsorption step. However, the concentration of the catalyst components in the elution liquid is particularly high in the initial period of the elution. Moreover, the reverse mixing of the elution liquid and the mother liquid cannot be prevented completely. Naturally, the mother liquor can be purged only to a limited extent.

Therefore, when the mother liquor remaining in the resin layer is discharged to the outside of the system with an inert gas and the elation is started thereafter, the mother liquor remained in the resin layer is completely replaced with the inert gas, and an elution liquid having a high concentrations of metal ions and bromine ion can be obtained.

To summarize the advantage obtained by the present invention, cobalt and manganese which are valuable substances used in the liquid phase oxidation of an aromatic compound substituted with alkyl groups can be efficiently recovered and recycled by using a chelate resin of an anion exchange type.

The present invention has the following characteristics as the process for recovering the metal components of the catalyst and enables the industrially advantageous recovery of metal components of the catalyst.

(1) An alkali metal carbonate or oxalic acid which is required in processes for recovery of the metal components in the form of carbonates or oxalates is not necessary, and complicated operations such as neutralization, precipitation and separation are not necessary either.

(2) An exceedingly high ratio of bromine to metals is not necessary. Therefore, loss of bromine compounds can be reduced, and the possibility of corrosion decreases.

(3) A highly concentrated liquid for recycling can be obtained, and the metal components of the catalyst can be recovered efficiently by setting different temperatures for the mother liquor of the oxidation at the time of adsorption of the catalyst components and for the elation liquid at the time of recovery of the catalyst components, by passing the mother liquor of the oxidation and the elution liquid through the anion exchange resin in the directions opposite to each other, and by purging the mother liquor remaining in the resin layer to the outside of the system before the elution.

EXAMPLES

The present invention is described more specifically with reference to examples. However, the present invention is not limited to the examples.

In the following Examples and Comparative Examples, an ion exchange column of double glass tubes was packed with 150 ml of an anion exchange resin and heat insulated by circulation of water of the same temperature as that of a liquid supplied into the column so that the temperature of the supplied liquid is not affected by the outside temperature.

In Examples 1 to 6, the ion exchange resin was pretreated by passing 200 ml of a solution of acetic acid containing 10% by weight of hydrobromic acid through the resin to convert the resin into the bromide form, followed by passing a solution of acetic acid containing 20% by weight of water through the resin to remove excess hydrobromic acid. A solution of acetic acid containing 50% by weight of water was used as the elation liquid.

EXAMPLE 1

A reaction product obtained by the liquid phase oxidation of pxylene in acetic acid was cooled to 80° C., and a mother liquor of the oxidation was obtained after the solid-liquid separation of the resultant product using a vacuum filter. The mother liquor was used as the raw material liquid in the recovery process. This raw material liquid contained 700 ppm of cobalt and 400 ppm of manganese and had a ratio bromine/(cobalt+manganese) of 0.67.

An ion exchange column was packed with 150 ml of a chelate resin of an anion exchange type (manufactured by SUMITOMO CHEMICAL Co., Ltd.; CR-2) which had been pretreated as described above, and hot water adjusted to 80° C. was circulated through a jacket of the column. The raw material liquid in an amount of 1,500 g was introduced into the ion exchange column downward from the upper part of the column. The liquid for treatment which had passed through the column was discharged into a waste liquid tank. Then, water adjusted to 30° C. was circulated through the jacket of the column, and the elution liquid adjusted to 30° C. was supplied upward from the lower part of the ion exchange column until the concentration of cobalt at the outlet of the ion exchange column reached 10 ppm or less.

The yield of recovery of cobalt was 99.5%, and the yield of recovery of manganese was 80%. The amount of the liquid required for the elution was 450 g.

EXAMPLE 2

The same procedures as those conducted in Example 1 were conducted except that the temperature of the jacket during the elution was kept at 60° C. The amount of the liquid required for the elution to obtain the same yields of recovery as those in Example 1 was 500 g.

EXAMPLE 3

The same procedures as those conducted in Example 1 were conducted except that the temperature of the jacket during the elution was kept at 80° C. The amount of the liquid required for the elution to obtain the same yields of recovery as those in Example 1 was 750 g.

EXAMPLE 4

The same procedures as those conducted in Example 1 were conducted except that the direction of the flow of the mother liquor during the adsorption was the same as that of the elution liquid, i.e., upward through the column. The amount of the liquid required for the elution to obtain the same yields of recovery as those in Example 1 was 910 g.

EXAMPLE 5

The same procedures as those conducted in Example 1 were conducted except that the liquid inside the column was purged to the outside of the system with nitrogen after the adsorption, and then the elution liquid was supplied upward. The amount of the liquid required for the elution to obtain the same yields of recovery as those in Example 1 decreased to 400 g.

EXAMPLE 6

A reaction product obtained by the liquid phase oxidation of 2,6-dimethylnaphthalene in acetic acid was cooled to 80° C., and a mother liquor of the oxidation was obtained after the solid-liquid separation of the resultant product using a decanter type centrifuge. The mother liquor was kept at 80° C. and used as the raw material liquid in the recovery process. This raw material liquid contained 1,600 ppm of cobalt and 1,000 ppm of manganese and had a ratio bromine/(cobalt+manganese) of 0.83.

An ion exchange column was packed with 150 ml of a chelate resin of an anion exchange type (manufactured by SUMITOMO CHEMICAL Co., Ltd.; CR-2) which had been pretreated as described above, and hot water adjusted to 80° C. was circulated through a jacket of the column. The raw material liquid in an amount of 600 g was introduced into the ion exchange column downward from the upper part of the column. The liquid for treatment which had passed through the column was discharged into a waste liquid tank. Then after the liquid remaining in the ion exchange column after the adsorption was removed with nitrogen gas to the outside of the system, water adjusted to 30° C. was circulated through the jacket of the column, and the elution liquid adjusted to 30° C. was supplied upward from the lower part of the ion exchange column until the concentration of cobalt at the outlet of the ion exchange column reached 10 ppm or less.

The yield of recovery of cobalt was 99.3%, and the yield of recovery of manganese was 80%. The amount of the liquid required for the elution was 400 g.

EXAMPLE 7

A reaction product obtained by the liquid phase oxidation of 2,6-dimethylnaphthalene in acetic acid was cooled to 80° C., and a mother liquor of the oxidation was obtained after the solid-liquid separation of the resultant product using a decanter type centrifuge. Hydrobromic acid was added to the mother liquor to prepare a liquid for treatment supplied to the ion exchange column [bromine/(cobalt+manganese)= 1.2]. The composition of this liquid is shown in Table 1. The liquid for treatment was kept at 80° C. and used in the next catalyst recovery step.

An ion exchange column was packed with 150 ml of a resin of a strong basic ion exchange type (manufactured by ORGANO Co., Ltd.; IRA-900) which had been pretreated as described above, and hot water adjusted to 80° C. was circulated through a jacket of the column. The adsorption step for 270 minutes and the elution step for 90 minutes were successively repeated as follows:

In the adsorption step, the liquid for treatment was introduced into the column downward from the upper part of the column at the speed of 400 ml/hour for 270 minutes. The liquid for treatment which had passed through the ion exchange column was discharged into a waste liquid tank.

In the elution step, an elution liquid, which was acetic acid containing about 30% by weight of a condensate separated from the reflux cooler of the reactor of the oxidation, was introduced into the ion exchange column upward from the lower part of the column at the speed of 400 ml/hour for 90 minutes. The elution liquid which had passed through the ion exchange column was discharged into a recovery liquid tank.

The above operations were carried out continuously for 90 days. The operations in the above steps could be conducted without any problem. The yields of recovery of the components after 3 days and 90 days of the test are shown in Table 1.

TABLE 1

|  | composition of liquid | yield of recovery | |
| --- | --- | --- | --- |
|  | for treatment (ppm) | after 3 days (%) | after 90 days (%) |
| cobalt | 680 | 97 | 95 |
| manganese | 2380 | 51 | 45 |
| bromine | 5250 | 95 | 94 |

EXAMPLE 8

The same reaction product as that used in Example 7, i.e., the reaction product obtained by the liquid phase oxidation of 2,6-dimethylnaphthalene in acetic acid, was cooled to 100° C., and a mother liquor of the oxidation was obtained after the solid-liquid separation of the resultant product using a decanter type centrifuge. Hydrobromic acid was added to the mother liquor to prepare a liquid for treatment. The liquid for treatment was kept at 100° C. and used in the next catalyst recovery step.

An ion exchange column was packed with 150 ml of a resin of a weak basic ion exchange type (manufactured by ORGANO Co., Ltd.; IRA-96SB) which had been pretreated as described in Example 7, and hot water adjusted to 97° C. was circulated through a jacket of the column. The adsorption step for 270 minutes and the elution step for 90 minutes were successively repeated as follows:

In the adsorption step, the liquid for treatment was introduced into the column downward from the upper part of the column at the speed of 400 ml/hour for 270 minutes. The liquid for treatment which had passed through the ion exchange column was discharged into a waste liquid tank.

In the elution step, the same elution liquid as that used in Example 7 was introduced into the ion exchange column upward from the lower part of the column at the speed of 400 ml/hour for 90 minutes. The elution liquid which had passed through the ion exchange column was discharged into a recovery liquid tank.

The above operations were carried out continuously for 90 days. The operations in the above steps could be conducted without any problem. The yields of recovery of the components after 3 days and 90 days of the test are shown in Table 2.

TABLE 2

| | yield of recovery | |
|---|---|---|
| | after 3 days (%) | after 90 days (%) |
| cobalt | 99 | 98 |
| manganese | 54 | 51 |
| bromine | 96 | 93 |

COMPARATIVE EXAMPLE 1

The same procedures as those conducted in Example 7 were conducted except that, in the elution step, the elution liquid was introduced into the ion exchange column downward from the upper part of the column similarly to the adsorption step. In other words, the direction of flow of the liquid was the same in the adsorption step and the elution step in Examples 7 and 8, while the direction of flow of the liquid was opposite in the adsorption step and the elution step in Examples 7 and 8.

After the operation was continued for some time, fine crystals contained in the liquid for treatment were accumulated on the ion exchange resin. After 2 days of the operation, difference in the pressure at the two sides of the resin layer increased, and the operation could not be continued.

COMPARATIVE EXAMPLE 2

The same procedures as those conducted in Example 7 were conducted except that the temperature of water circulated through the jacket was adjusted to 25° C., and the operation was continued for 3 days. The result is shown in Table 3.

TABLE 3

| | yield of recovery after 3 days (%) |
|---|---|
| cobalt | 55 |
| manganese | 13 |
| bromine | 37 |

What is claimed is:

1. A process for continuously producing an aromatic carboxylic acid comprising oxidizing an aromatic compound substituted with alkyl groups with molecular oxygen gas in the liquid phase in a solvent containing a lower aliphatic carboxylic acid in the presence of a catalyst comprising heavy metal compounds and a bromine compound, wherein a mother liquor which is obtained after removal of crystals from a reaction liquid of the liquid phase oxidation and contains heavy metal ions and bromine ion as catalyst components is brought into contact with a chelate resin of an anion exchange type, and subsequently, the catalyst components are recovered with an elution liquid.

2. A process according to claim 1, wherein the mother liquor is brought into contact with the chelate resin at a temperature of 50° to 120° C., and the elution liquid is brought into contact with the chelate resin at a temperature of 20° to 60° C.

3. A process according to claim 1, wherein the mother liquor is brought into contact with the chelate resin of an anion exchange type in an ion exchange column so that the heavy metal ions and the bromine ion of the catalyst components are adsorbed with the chelate resin, and subsequently, the elution liquid is passed through the ion exchange column in the direction opposite to the direction of the mother liquor so that the catalyst components are recovered.

4. A process according to claim 3, wherein the mother liquor is passed through the ion exchange column downward from an upper part thereof so that the heavy metal components and the bromine ion of the catalyst components are adsorbed with the chelate resin, and subsequently the elution liquid is passed through the ion exchange column upward from a lower part thereof so that the catalyst components are recovered.

5. A process according to claim 1, wherein, after the mother liquor is brought into contact with the chelate resin of an anion exchange type so that the heavy metal ions and the bromine ion are adsorbed with the chelate resin, the liquid remaining in a layer of the chelate resin is replaced with an inert gas.

6. A process according to claim 1, wherein the elution liquid is a solution of acetic acid containing 15% by weight or more of water.

7. A process according to claim 1, wherein a condensate separated in a reflux cooler of an oxidation reactor for the liquid phase oxidation is used as the elution liquid.

8. A process according to claim 1, wherein the aromatic compound substituted with alkyl groups is 2,6-dimethylnaphthalene, and the aromatic carboxylic acid produced by the process is 2,6-naphthalenedicarboxylic acid.

9. A process for continuously producing 2,6-naphthalenedicarboxylic acid comprising oxidizing a 2,6-dialkylnaphthalene with molecular oxygen gas in the liquid phase in a solvent containing a lower aliphatic carboxylic acid in the presence of a catalyst comprising heavy metal compounds and a bromine compound, wherein a mother liquor which is obtained after removal of crystals from a reaction liquid of the liquid phase oxidation and contains heavy metal ions and bromine ion as catalyst components is brought into contact with an anion exchange resin at 50° to 120° C., and subsequently, the catalyst components are recovered by passing an elution liquid through the resin in a direction opposite to the direction of the mother liquor at 20° to 60° C.

* * * * *